(12) United States Patent
Zhao et al.

(10) Patent No.: US 9,555,123 B2
(45) Date of Patent: Jan. 31, 2017

(54) MULTI-ARM POLYETHYLENE GLYCOL DERIVATIVES, CONJUGATES AND GELS OF PHARMACEUTICALS AND THE SAME

(75) Inventors: Xuan Zhao, Tianjin (CN); Meina Lin, Tianjin (CN)

(73) Assignee: JENKEM TECHNOLOGY CO., LTD. TIANJIN BRANCH, Tianjin (CN)

( * ) Notice: Subject to any disclaimer, the term of this patent is extended or adjusted under 35 U.S.C. 154(b) by 193 days.

(21) Appl. No.: 13/518,940

(22) PCT Filed: Dec. 23, 2010

(86) PCT No.: PCT/CN2010/002139
§ 371 (c)(1),
(2), (4) Date: Jul. 27, 2012

(87) PCT Pub. No.: WO2011/075953
PCT Pub. Date: Jun. 30, 2011

(65) Prior Publication Data
US 2012/0282671 A1    Nov. 8, 2012

(30) Foreign Application Priority Data
Dec. 25, 2009   (CN) .......................... 2009 1 0259749

(51) Int. Cl.
| | |
|---|---|
| C08G 65/34 | (2006.01) |
| C08G 65/48 | (2006.01) |
| A61K 47/48 | (2006.01) |
| C08G 65/26 | (2006.01) |
| C08G 65/329 | (2006.01) |
| C08G 65/332 | (2006.01) |
| A61K 31/727 | (2006.01) |
| C08G 65/333 | (2006.01) |

(52) U.S. Cl.
CPC ....... *A61K 47/48215* (2013.01); *A61K 31/727* (2013.01); *A61K 47/48784* (2013.01); *C08G 65/2609* (2013.01); *C08G 65/329* (2013.01); *C08G 65/3322* (2013.01); *C08G 65/33337* (2013.01); *C08G 2650/24* (2013.01); *C08L 2203/02* (2013.01)

(58) Field of Classification Search
CPC .................. A61K 47/48215; C08G 65/2621; C08G 65/33393
See application file for complete search history.

(56) References Cited

U.S. PATENT DOCUMENTS

| | | | | |
|---|---|---|---|---|
| 5,728,895 A | * | 3/1998 | Wiggins et al. | ............ 568/601 |
| 2004/0096507 A1 | | 5/2004 | Kwang et al. | |
| 2006/0275252 A1 | | 12/2006 | Harris et al. | |
| 2007/0031371 A1 | * | 2/2007 | McManus et al. | ........ 424/78.37 |
| 2008/0039547 A1 | | 2/2008 | Khatri et al. | |
| 2009/0324720 A1 | | 12/2009 | He et al. | |
| 2011/0200550 A1 | * | 8/2011 | Kozlowski et al. | ....... 424/78.17 |
| 2011/0286956 A1 | | 11/2011 | Zhao et al. | |

FOREIGN PATENT DOCUMENTS

| | | |
|---|---|---|
| CN | 1706865 A | 12/2005 |
| CN | 101724144 A | 6/2010 |
| WO | 2004/050029 A2 | 6/2004 |
| WO | 2009/132153 A2 | 10/2009 |

* cited by examiner

*Primary Examiner* — Jessica Worsham
(74) *Attorney, Agent, or Firm* — Jun He Law Offices P.C.; James J. Zhu

(57) ABSTRACT

A multi-arm polyethylene glycol (I) having different kinds of reactive groups and the uses thereof are disclosed, which is formed by polymerizing ethylene oxide with oligo-pentaerythritol as an initiator, wherein, PEG is same or different and is —(CH2CH2O)m-, the average value of m is an integer of 2-250; l is an integer of 1 or more. The method for producing the multi-arm polyethylene glycol having different kinds of reactive groups, the multi-arm polyethylene glycol active derivatives comprising linking groups X attached to PEG and terminal reactive groups F attached to X, the gels formed by the multi-arm polyethylene glycol active derivatives, the drug conjugates formed by the multi-arm polyethylene glycol active derivatives and drug molecules, and the uses thereof in preparing drugs are also disclosed.

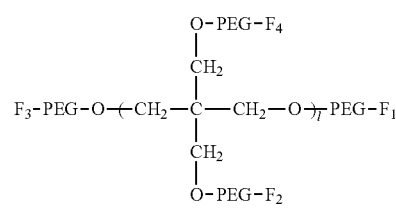

2 Claims, No Drawings

MULTI-ARM POLYETHYLENE GLYCOL DERIVATIVES, CONJUGATES AND GELS OF PHARMACEUTICALS AND THE SAME

TECHNICAL FIELD

The present invention relates to the multi-arm polyethylene glycol derivatives with different kinds of active groups and their preparation methods, drug molecules conjugates and the gel materials. The invention also relates to the role of the described above new multi-arm polyethylene glycol derivatives with different types of active groups and its gels in the preparation of pharmaceutical preparations and medical device materials.

BACKGROUND ART

At present, the polyethylene glycol derivatives are widely used in combination with proteins, peptides, and other therapeutic agents to extend the physiological half-life of drugs referred to, reduce immunogenicity and toxicity. In clinical use, PEG and its derivatives which act as the carrier in the production of pharmaceutical preparations have been widely used in lots of medicines. The attempts to bond PEG to the drug molecules have also seen significantly development in the past decade, and widely used in many approved medicines such as PEGASYS® (peginterferon alfa-2a, which is a combination of α-interferon and polyethylene glycol with a longer circulation half-life and a better therapeutic effect. Metabolic processes of polyethylene glycol in the human body have been quite clear, which is a safe synthetic polymer material without side effects.

In terms of drug modification, the latest research direction is to connect a targeted molecule to the drug molecules through polyethylene glycol to enrich drug molecules near the focus, so as to achieve the best therapeutic effect. For example, anticancer medicine is connected to monoclonal antibodies. According to the recent research of our company, the combination of two different medicinal molecules through polyethylene glycol can maintain the aforementioned increase of physiological half-life and reduce immunogenicity and toxicity, while giving full play to the two molecules' synergies. Intermolecular synergy is very important in the Chinese medicine theory. When two or more different molecules are connected with polyethylene glycol, a PEG derivative with metachronous double functional groups is needed. Currently, our company could be able to produce a variety of PEG derivatives with metachronous double functional groups, such as MAL-PEG-NHS, acrylic acid-PEG-NHS, and HO-PEG-COOH. However, those PEG derivatives with metachronous double functional groups are straight-chain polyethylene glycol derivatives.

Straight-chain polyethylene glycol derivatives with metachronous double functional groups are limited to some extent in applications. The ratio of two molecules connected by the straight-chain ethylene glycol derivatives with metachronous double functional groups is basically 1:1. If one molecule is needed more than another one, for example, if one molecule has with low in vivo activity, more connections will be required for the low activity molecules than the high-activity molecules, which is a challenge to the straight-chain polyethylene glycol derivatives with metachronous double functional groups. At the same time, in terms of drug carrying, multi-arm polyethylene glycol is advantageous over the straight-chain polyethylene glycol. Straight-chain polyethylene glycol derivatives with metachronous double functional groups can only carry two molecules, while the multi-arm polyethylene glycol has several end groups, and thus has more than one drug connection points, and can carry several drug molecules. At present, multi-arm polyethylene glycol is widely used in the PEG-modification of peptides and small molecule drugs. However, the multi-arm PEG derivatives on the market only have the same active groups such as 4-arm polyethylene glycol succinate —NHS ester, (4arm-SS). The U.S. Pat. No. 6,046,305 shows a star-shaped polyethylene glycol derivative formed through polymerization reaction with only one active group. At the same time, one arm of this star-shaped polyethylene glycol derivative is connected with the other arms through the non-ether bond, such as the amide bond or ester bond. This connection is different in the way, and can reduce the stability of the derivatives.

BRIEF SUMMARY OF THE INVENTION

The purpose of this invention is to increase the kinds of active groups of the multi-arm polyethylene glycol in the existing technology by providing a new, simple structure and stable multi-arm polyethylene glycol derivatives with different types of active groups. The new multi-arm PEG derivatives with different types of active groups include metachronous double functional groups polyethylene glycol derivatives and metachronous three functional groups polyethylene glycol derivatives. At the same time, the invention provides a new preparation method for the multi-arm PEG derivatives with different types of active groups and conjugates of multi-arm polyethylene glycol active polyethylene glycol derivatives and pharmaceutical molecules and gels and their applications.

CONTENTS OF INVENTION

The invention provides a novel multi-arm polyethylene glycol derivative, which has the structure of general formula I:

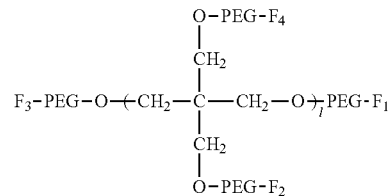

wherein:

$F_1$, $F_2$, $F_3$ and $F_4$ each has a structure of —X—Y, and at least two of $F_1$, $F_2$, $F_3$ and $F_4$ are different;

X is a linking moiety, which is selected from a group consisting of: $(CH_2)_i$, $(CH_2)_i NH$, $(CH_2)_i OCOO$—, $(CH_2)_i OCONH$—, $(CH_2)_i NHCOO$—, $(CH_2)_i NHCONH$—, $OC(CH_2)_i COO$—, and $(CH_2)_i CONH$—; i is an integer between 0 and 10;

Y is a functional end group, which is selected from a group consisting of: hydroxyl, amino, mercapto, carboxyl, ester group, aldehyde group, acrylic group and maleimide group;

PEG is the same or different —$(CH_2CH_2O)_m$—, the average value m is an integer between 2 and 250;

l is an integer ≥1.

In a preferred embodiment, $F_1$ in the multi-arm polyethylene glycol derivatives of the invention is —X—COOH;

$F_2$, $F_3$ and $F_4$ each has the structure of —X—Y and at least one of $F_2$, $F_3$ and $F_4$ is not —X—COOH. The described active derivatives of multi-arm polyethylene glycol have the structure of the formula II:

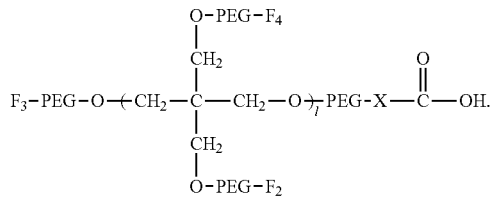

II

In a preferred embodiment, $F_1$ and $F_2$ in the multi-arm polyethylene glycol derivatives of the invention are both —X—COOH; $F_3$ and $F_4$ each has the structure of —X—Y and at least one of $F_3$ and $F_4$ is not —X—COOH. The described active derivatives of multi-arm polyethylene glycol have the structure of the formula IIA:

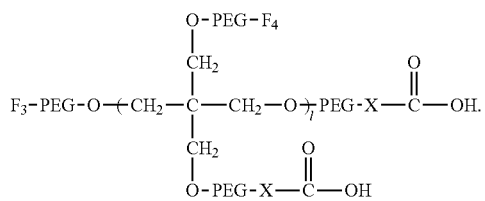

IIA

In a detailed embodiment, the described multi-arm polyethylene glycol derivative has the multi-arm polyethylene glycol hydroxy-single-acetic acid of the structure of the formula III:

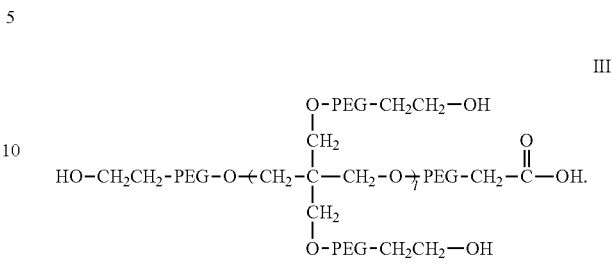

III

In a detailed embodiment, the described multi-arm polyethylene glycol derivative has the multi-arm polyethylene glycol hydroxy-multi-acetic acid of the formula IIIA as follows:

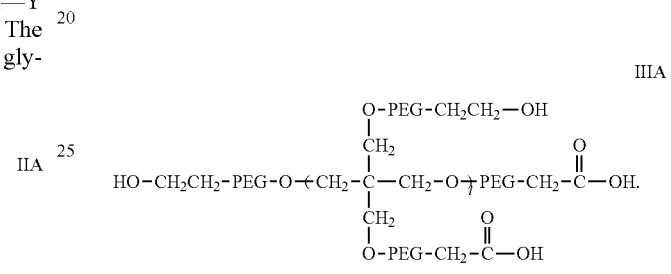

IIIA

In a detailed embodiment, the described multi-arm polyethylene glycol derivative has the multi-arm polyethylene glycol hydroxy-single-NHS ester of the formula IV as follows:

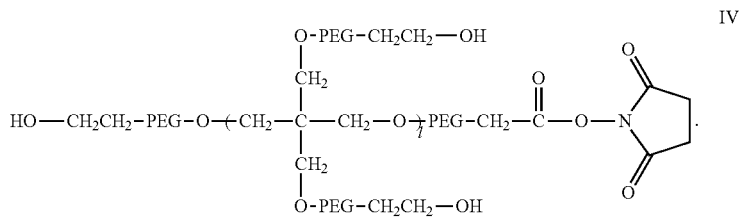

IV

In a detailed embodiment, the described multi-arm polyethylene glycol derivative has the multi-arm polyethylene glycol hydroxy-multi-NHS ester of the structure of the formula IVA as follows:

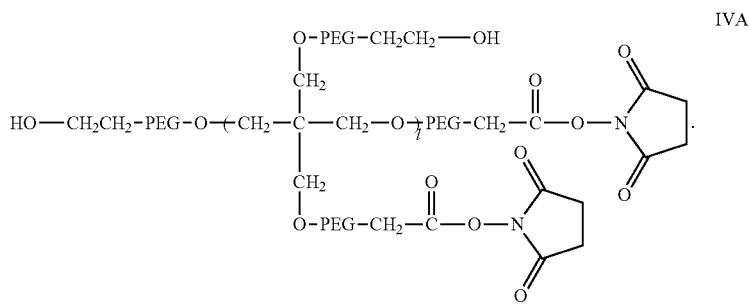

IVA

In a detailed embodiment, the described multi-arm polyethylene glycol derivative has the multi-arm polyethylene glycol amino-single-acetic acid of the structure of the formula V as follows:

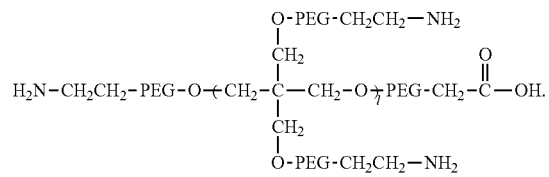

V

In a detailed embodiment, the described multi-arm polyethylene glycol derivative has the multi-arm polyethylene glycol amino-multi-acetic acid of the structure of the formula VA as follows:

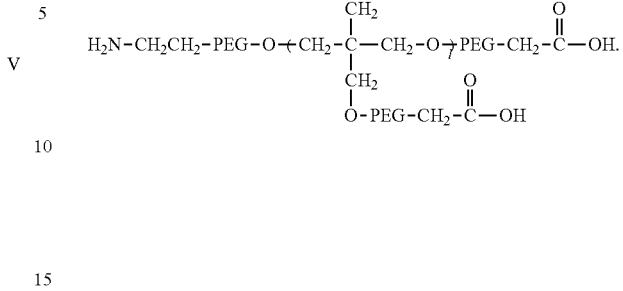

VA

In a detailed embodiment, the described multi-arm polyethylene glycol derivative has the multi-arm polyethylene glycol maleimide-single-NHS ester of the structure of the formula VI as follows:

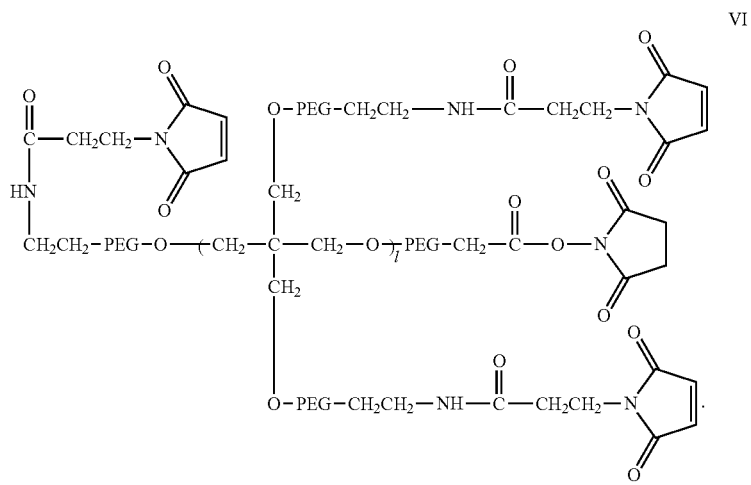

VI

In a detailed embodiment, the described multi-arm polyethylene glycol derivative has the multi-arm polyethylene glycol maleimide-multi-NHS ester of the structure of the formula VIA as follows:

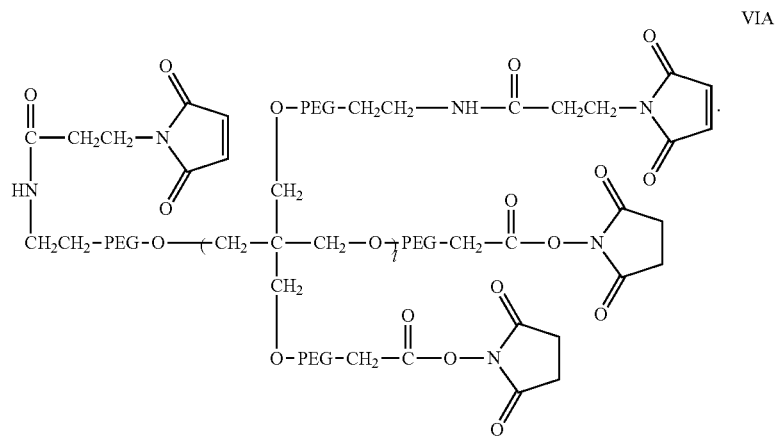

VIA

In a detailed embodiment, the described multi-arm polyethylene glycol derivative has the multi-arm polyethylene glycol acrylate-single-NHS ester of the structure of the formula VII as follows:

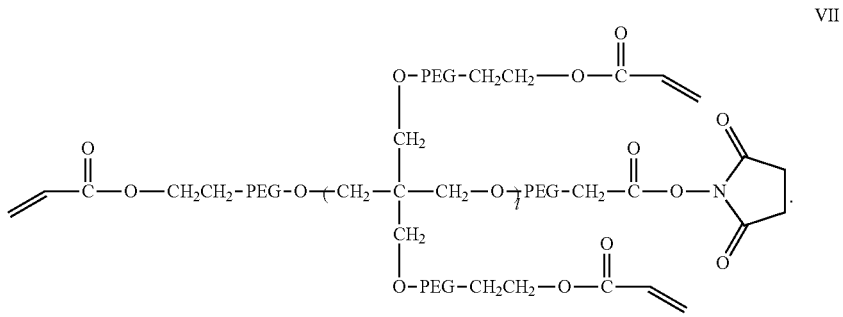

VII

In a detailed embodiment, the described multi-arm polyethylene glycol derivative has the multi-arm polyethylene glycol acrylate-multi-NHS ester of the structure of the formula VIIA as follows:

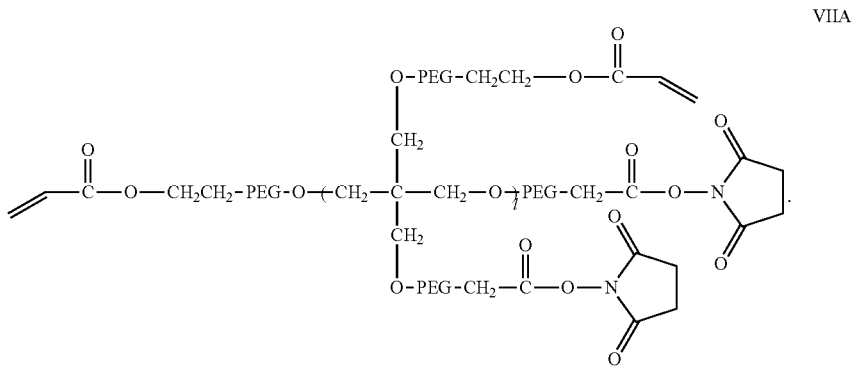

VIIA

In a preferred embodiment, the l in the described multi-arm polyethylene glycol derivatives is an integer between 1 and 10 (including 1 and 10) and the further preferred l is an integer between 1 and 3 (including 1 and 3).

In a preferred embodiment, the molecular weight of the described multi-arm polyethylene glycol is 400-80000 Dalton, preferred 1000-20000 Dalton.

The present invention also provides the conjugates formed from the active derivatives of the described multi polyethylene glycol and pharmaceutical molecules through the end group F of the active derivatives. In some embodiments, the specified pharmaceutical molecules are selected from the groups consisting of: amino acids, proteins, enzymes, nucleosides, saccharides, organic acids, flavonoids, quinones, terpenoids, benzene phenols, steroidal and glycosides thereof, alkaloids, and the combinations thereof.

Preferably, the present invention provides a conjugate formed from the eight-arm polyethylene glycol acid and the Irinotecan or docetaxel.

The invention also provides a gel made from the active derivative of the described active multi-arm polyethylene glycol.

The present invention further provides the applications of the above conjugates in pharmaceutical preparation.

The present invention further provides the method of preparing the new, simple and stable multi-arm PEG derivatives with different types of active groups. The described methods include: use the pentaerythritol or oligomer pentaerythritol as the initiator to polymerize 20 ethylene oxide and produce multi-arm polyethylene glycol, convert one or more end hydroxy groups of the multi-arm polyethylene glycol into carboxylic acid or amine via chemical reaction, then isolate and purify the single-carboxyl or multi-more carboxyl, single-amino or multi-amino products with ion exchange column, and then transform the corresponding hydroxyl, carboxyl and amino groups into the desired reactive groups through the chemical reaction, and finally produce the multi-arm polyethylene glycol derivatives with different types of active groups described in the innovation.

DESCRIPTION OF THE INVENTION

The method of preparing multi-arm polyethylene glycol derivatives with different types of active groups is described with the following examples:

The structural formula of multi-arm PEG chain is as follows:

wherein:

R is the central molecule or the non-molecular hydroxyl part of the initiator molecules, which is typically the alkyl, cycloalkyl or aralkyl;

n is the number of branches or the number of arms;

PEG is the same or different $-(CH_2CH_2O)_m-$, m is any integer, characterizing the single-arm polymerization degree of polyethylene glycol.

When R is the non-hydroxyl part of pentaerythritol, the initiator molecule is pentaerythritol, and the chemical structure is as follows:

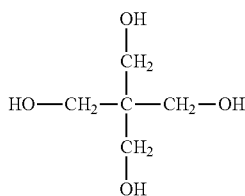

wherein:

n is 4, and what is formed is the four-arm polyethylene glycol.

When R is the non-hydroxyl part of dimerization of pentaerythritol, the initiator molecule is dimerization of pentaerythritol with the following chemical structure:

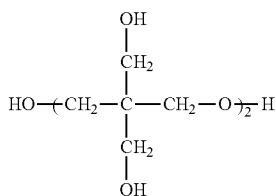

wherein:

n is 6, and what is formed is the six-arm polyethylene glycol.

When R is the non-hydroxyl part of trimeric pentaerythritol, the initiator molecule is trimeric pentaerythritol with the following chemical structure:

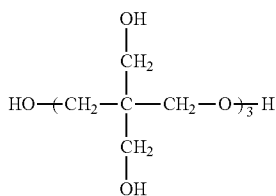

wherein:

n is 8, and what is formed is the eight-arm polyethylene glycol.

The multi-arm polyethylene glycol used in the invention is produced by polymerizing 5 ethylene oxide with the above pentaerythritol or oligomer pentaerythritol as the initiator.

The polyethylene glycol could be represented with molecular weight generally as long as one arm's molecular weight of the polyethylene glycol is between 300 and 60,000 Daltons, which is equivalent to m being about 6 to 1300. More preferably, m is 28,112 and 450, respectively corresponding to a molecular weight of 1,325, 5,000 and 20,000. Due to potential uneven nature of the initial PEG compounds usually limited by its average molecular weight but not the repeating units, the molecular weight is preferred to characterize polyethylene glycol polymer instead of using the integer m to represent the self-repeating units in the PEG polymer.

Active Groups:

When using the active derivatives of the multi-arm polyethylene glycol of the invention, different purposes of the derivatives are determined by the different end functional groups F. The introduction of these functional groups will determine the application areas and applicable structures of the derivatives. The most common functional groups is N-hydroxysuccinimide ester (NHS), as can be seen in formula IV. The active derivatives with the NHS ester structure can be linked with the groups with amine.

Similarly, according to this manual, the technical personnel in the field can obtain the multi-arm active polyethylene glycol derivatives with amino functional groups, as can be seen in formula III.

Similarly, the technical personnel in the field can obtain the multi-arm active polyethylene glycol derivatives with carboxyl functional groups, as can be seen in formula IV.

Similarly, the technical personnel in the field can obtain the multi-arm active polyethylene glycol derivatives with Maleimide functional groups (MAL), as can be seen in formula VI. The active derivatives with MAL structure can be linked with the thiol groups.

Many medicines contain such functional groups as active amino, carboxyl and hydroxyl, which could combine with monosaccharides, polysaccharides, nucleosides, polynucleoside phosphoryl and other ingredients in vivo to form active pharmacology structure in organisms.

Therefore, the PEG derivatives with the modified functional groups can be combined with these medicine molecules in the same way to replace bio-organic molecules, so as to overcome such shortcomings as the short half-life and short-time physiological efficacy of bio-organic molecules in vivo.

Active derivatives of multi-arm polyethylene glycol of the invention could be combined with drug molecules through appropriate end functional groups (F). The described end functional groups can connect the free amino groups, hydroxyl, sulfur hydroxyl in proteins, peptides or other natural medicines with PEG derivatives. For small molecule medicines, each multi-arm PEG molecule can bond several medicine molecules. Such PEG derivatives have relatively high drug load to secure the appropriate concentration of the drug and enhance the release function, so as to improve the physiological role of the drug molecules in the body.

The purpose of all these applications is just to provide a possible reference model for the medical applications of the PEG derivatives, and the actual applications and selections shall be confirmed based on the pharmacological, toxicological and clinical tests.

In the combinations of the invention, some of the medicine molecules are preferred as amino acids, proteins, enzymes, nucleosides, sugars, organic acids, flavonoids, quinones, terpenes, phenolic phenylpropanoids, steroidal and its glycosides, alkaloids. Protein medicine molecules are preferred as interferon drugs, EPO drugs, growth hormone drugs, antibody drugs, and so on.

The combinations of the invention can be dosed in the form of a pure compound or suitable pharmaceutical compositions in any acceptable dosing method or with the reagents with the similar purposes. Therefore, the medicine could be taken through oral, nasal, rectal, transdermal or injection dosing method in the form of solid, semi-solid, lyophilized powder or liquid, for example, tablets, suppositories, pills soft and hard gelatin capsules, powders, solutions, suspensions, or aerosols, etc., and the unit dosage forms of accurate dose and simple dosing method shall be preferred. The combinations can include conventional pharmaceutical carriers or excipients and combinations of the invention, which are used as active ingredients (one or more). In addition, other drugs, carriers and auxiliary agents could also be included.

Typically, according to the desired dosing method, the pharmaceutically acceptable combinations will include the combinations of the invention in the weight % from 1 to about 99, and the suitable pharmaceutical excipient in the weight % from 99 to 1. The preferred combination contains about 5-75% of the combinations of the invention, and the remaining composition is the suitable pharmaceutical excipients.

The preferred dosing method is injection with conventional daily dose plan which can be adjusted according to the severity of the disease. Combinations of the invention or their pharmaceutically acceptable salts can also be made into the injection, such as dispersing about 0.5 to about 50% active ingredients in the pharmaceutical auxiliary agents that can be dosed in liquid, such as water, brine, aqueous glucose, glycerol, ethanol, etc., so as to form a solution or suspension.

For the pharmaceutical combinations that can be dosed in liquid, the combinations of the invention (about 0.5 to about 20%) and the selectively existing pharmaceutical adjuvants could be dispersed into carriers, such as water, saline, aqueous glucose, glycerol, ethanol, etc., to form a solution or suspension.

If necessary, the pharmaceutical combinations of the invention may also contain small amounts of auxiliary substances such as wetting agents or emulsifiers, pH buffers and anti-oxidants, for example: citric acid, sorbitan monolaurate, triethanolamine, oleic acidesters, butylated hydroxy toluene.

The actual preparation method of such formulations is publicly known by the technical personnel in the field, for example, it can be found at *Remington's Pharmaceutical Sciences,* 18th Edition (Mack Publishing Company, Easton, Pa., 1990). In any case, with the technology of the invention, the combinations used may contain a therapeutically effective combination for the treatment of the corresponding disease.

EXAMPLES

The following examples are offered to illustrate, but not to limit the present invention. All the reagents referred to in the following examples are commercially available unless otherwise indicated.

Example 1

Synthesis of 4-Arm Poly (Ethylene Glycol) Hydroxy—Single-Acetic Acid (III-1) and 4-Arm Poly(Ethylene Glycol) Hydroxy—Double-Acetic Acid (IIIA-1)

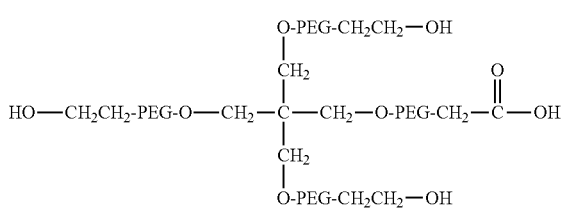

III-1

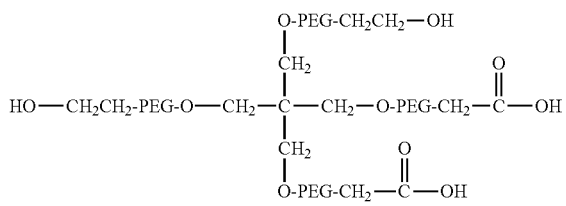

IIIA-1

Procedure:

4-ARM-PEG (10 kDa, 100 g) in 800 ml of TI-W was azeotropically dried by distilling off THF (20%) under nitrogen and the solution was cooled to room temperature. To the solution was added potassium tert-butoxide (4.48 g) and stirred 2 hours at room temperature. Tert-butyl bromoacetate (5.17 ml) was added dropwise and the mixture was stirred at room temperature overnight. The mixture was filtered and evaporated under vacuum to remove solvents. The residue was dissolved in a aqueous solution ($H_2O$ 500 mL+sodium hydroxide 8.16 g+sodium phosphate) and stirred 2 hours at 80° C. The PH of the aqueous solution was adjusted to about 2-3. Sodium chloride (15%) was added and the product was extracted with dichloromethane. The extract was dried over anhydrous sodium sulfate, filtered, concentrated under vacuum at 50° C., and then precipitated into diethyl ether. The filtrate was dried in vacuum and separated with DEAE ion-exchange chromatography column to afford 4-arm poly(ethylene glycol) hydroxy—single-acetic acid (III-1) and 4-arm poly(ethylene glycol) hydroxy—double-acetic acid (IIIA-1).

NMR (DMSO) δ: 4.01 (s, $CH_2COOH$), 4.54 (t, $CH_2OH$).

Example 2

Synthesis of Four-Arm Polyethylene Glycol Hydroxy—Single-N-hydroxysuccinimidyl Ester (IV-1)

IV-1

Procedure:

4-arm poly (ethylene glycol) hydroxy—single-acetic acid (III-1) (10 kDa, 0.5 g) and N-hydroxysiccinimide (0.01439 g) were dissolved in dichloromethane. DCC (0.01290 g) was added and the solution was stirred overnight at room temperature, filtered, concentrated under vacuum at 40° C. The residue was dissolved in hot iso-propanol and then crystallized by cooling the solution to 0° C. The resulting precipitate was collected, washed with iso-propanol and dried to afford the 4-arm poly(ethylene glycol) hydroxy—single-N-hydroxysuccinimidyl ester (IV-1).

NMR (DMSO) δ: 2.89 (s,

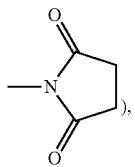

4.55 (t, CH$_2$CH$_2$OH).

Example 3

4-Arm Poly(Ethylene Glycol) Hydroxy—Single-Methyl Acetate (IVA-1)

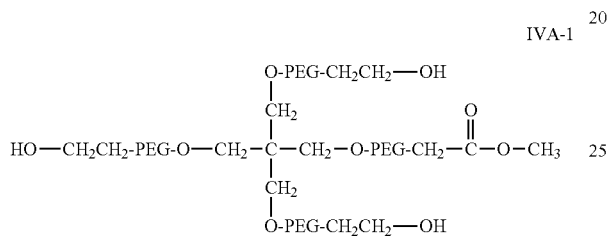

IVA-1

Procedure:

4-arm poly (ethylene glycol) hydroxyl—single-acetic acid (III-1) (10 kDa, 3.2 g) was dissolved in methanol (16 ml). The solution was cooled to 0° C. and the concentrated sulfuric acid was added drop wise. The solution was stirred 3 hours at room temperature. The solution was adjusted PH to about 7.0 with 8% NaHCO3 anqueous solution. The product was extracted with dichloromethane. The organic layer was separated, dried over anhydrous magnesium sulfate, filtered, and concentrated in 40° C., and then precipitated into diethyl ether. The filtrate was dried over vacuum to afford the four-arm poly(ethylene glycol) hydroxy—single methyl acetate (IVA-1).

NMR (DMSO) δ: 3.32 (s, CH$_2$COOCH$_3$), 4.13 (s, CH$_2$COOCH$_3$), 4.57 (t, CH$_2$OH).

Example 4

4-Arm Poly(Ethylene Glycol) Sulfonate—Single-Methyl Acetate (IVB-1)

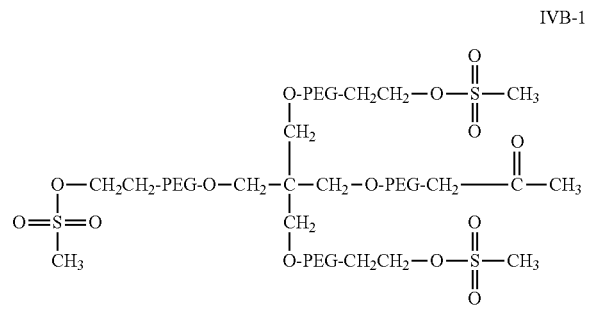

IVB-1

Procedure:

Four-arm poly(ethylene glycol) sulfonate—single methyl acetate (IVB-1) (10000, 3.0 g) in 50 ml of toluene was azeotropically dried by distilling off 38 ml toluene and the solution was cooled to room temperature. To the solution was added 5 ml of dichloromethane and 188 μl of triethylamine, 94 μl of MsCl was added dropwise. The solution was stirred at room temperature overnight and the reaction was quenched by adding 720 μl of absolute ethanol. The mixture was filtered, evaporated at 60° C. dissolved in hot iso-propanol and then crystallized by cooling the solution to 0° C. The resulting precipitate was collected, washed with iso-propanol and dried to afford the four-arm poly(ethylene glycol) sulfonate—single methyl acetate (IVB-1).

NMR (DMSO) δ: 3.17 (s, CH$_2$OSO$_2$CH$_3$), 4.13 (s, CH$_2$COOCH$_3$), 4.30 (t, CH$_2$OSO$_2$CH$_3$).

Example 5

4-Arm (Polyethylene Glycol) Amino—Single-Acetic Acid (V-1)

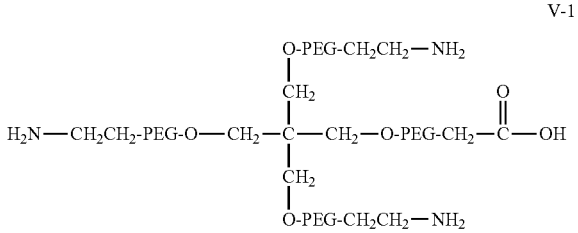

V-1

Procedure:

4-arm poly(ethylene glycol) sulfonate—single acetic acid (V-1) having a molecular weight of 10000 (2.6 g) was dissolved in 7.8 ml of water. The PH of the aqueous solution was adjusted to 12 with 2M sodium hydroxide and the solution was stirred 2-2.5 hours. Ammonia water (26 ml) and ammonium chloride (1.3 g) was added to the above aqueous solution. The mixture was stirred 72 hours at room temperature. Sodium chloride (7 g) was added and the reaction mixture was exacted with dichloromethane. The organic layer was collected and concentrated to remove the solvent at 40° C. Water (30 ml) and sodium chloride was then added and the PH of the aqueous solution was adjusted to 2-3 with 2M hydrochloric acid. The product was extracted with dichloromethane. The extract was dried with anhydrous sodium sulfate, concentrated and added to ethyl ether. The precipitated product was filtered off and dried under vacuum to offer the 4-arm poly(ethylene glycol) sulfonate—single acetic acid (V-1).

NMR (DMSO) δ: 2.96 (t, CH$_2$CH$_2$NH$_2$), 4.00 (s, CH$_2$COOH).

Example 6

4-Arm (Polyethylene Glycol) Hydroxy—Diethyl Methyl Ester (IVC-1)

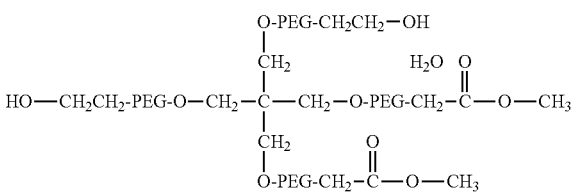

IVC-1

The initial material is 4-arm (polyethylene glycol) hydroxy—acetic acid (IIIA-1) with the molecular weight of 10,000, and its synthetic steps are same as that of Example 3.

NMR (DMSO) δ: 3.32 (s, $CH_2COOCH_3$), 4.13 (s, $CH_2COOCH_3$), 4.57 (t, $CH_2OH$).

Example 7

4-Arm (Polyethylene Glycol) Sulfonate—Diethyl Methyl Ester (IVD-1)

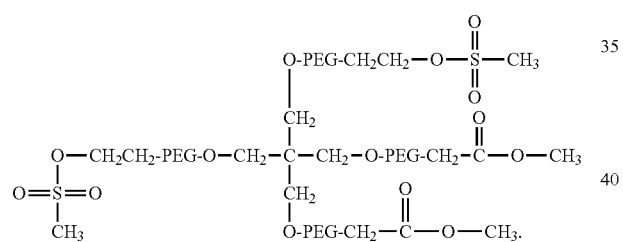

IVD-1

The initial material is 4-arm (polyethylene glycol) hydroxy—diethyl methyl ester (IVC-1) with the molecular weight of 10,000, and its synthetic steps are same as that of Example 4.

NMR (DMSO) δ: 3.17 (s, $CH_2OSO_2CH_3$), 3.32 (s, $CH_2COOCH_3$), 4.13 (s, $CH_2COOCH_3$), 4.30 (t, $CH_2OSO_2CH_3$).

Example 8

4-Arm polyethylene Glycol Amino—Double Acetic Acid (VA-I)

VA-1

The initial material is 4-arm (polyethylene glycol) sulfonate—diethyl methyl ester (IVD-1) with the molecular weight of 10,000, and its synthetic steps is same as that of Example 5.

NMR (DMSO) δ: 2.96 (t, $CH_2CH_2NH_2$), 4.00 (s, $CH_2COOH$).

Example 9

4-Arm (polyethylene Glycol)—Three Maleimide—Single-Acetic Acid (VB-1)

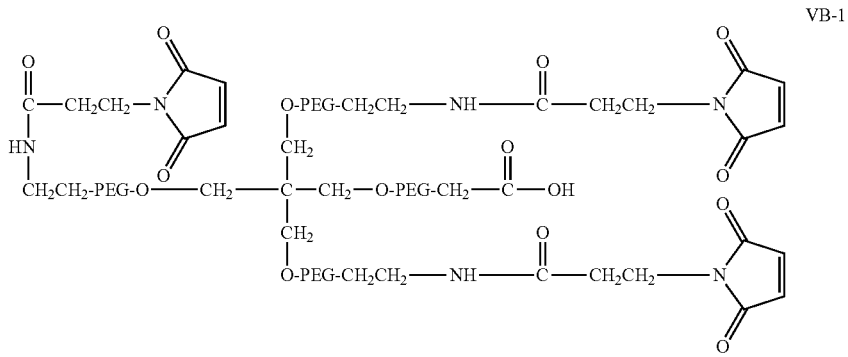

VB-1

Procedure:

4-arm poly(ethylene glycol) amino—single acetic acid (V-1) having a molecular weight of 10000 (1.0 g) was dissolved in 10 ml of dichloromethane. 42 ul of triethylam ine was added and then MAL-NHS 5 minutes later. The mixture was stirred overnight at room temperature avoiding light. The reaction solution was concentrated at 40. The residue was dissolved in hot isopropanol and then precipitated by cooling in an ice bath. The precipitate was filtered, washed by isopropanol and dried over vacuum to offer the 4-arm poly (ethylene glycol) three maleimide—single acetic acid (V-1).

NMR (DMSO) δ: 2.32 (t, CH$_2$CH$_2$NH$_2$), 4.01 (s, CH$_2$COOH), 7.00 (s,

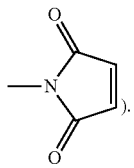

).

solvent. The residue was dissolved in hot isopropanol and then precipitated by cooling in an ice bath. The precipitate was filtered, washed by isopropanol and dried over vacuum to offer 4-arm poly(ethylene glycol)—three maleimide—single-succinimide ester (VI-1).

NMR (DMSO) δ: 2.83 (s,

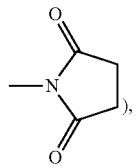

), 4.60 (s, CH$_2$COO), 7.00 (s,

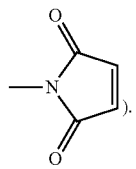

).

Example 10

4-Arm (Polyethylene Glycol)—Three Maleimide—Single-NHS Ester (VI-1)

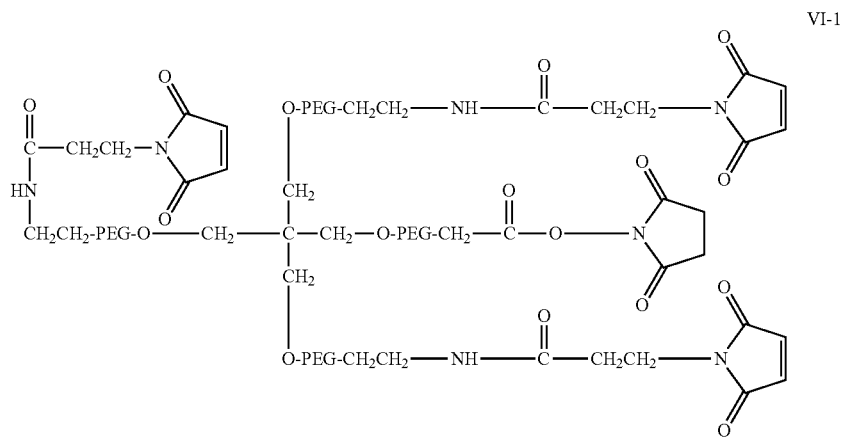

VI-1

Procedure:

4-arm poly (ethylene glycol)—three maleimide—single-acetic acid (VB-1) (10000, 1.0 g) and N-hydroxyl succinimide (0.01496 g) was dissolved in 10 ml of dichloromethane, DCC (0.02889 g) was added and the solution was stirred overnight at room temperature avoid light. The reaction mixture was filtered, concentrated to remove the

Example 11

4-Arm (Polyethylene Glycol)—Bimaleimide—Acetic Acid (VC-1)

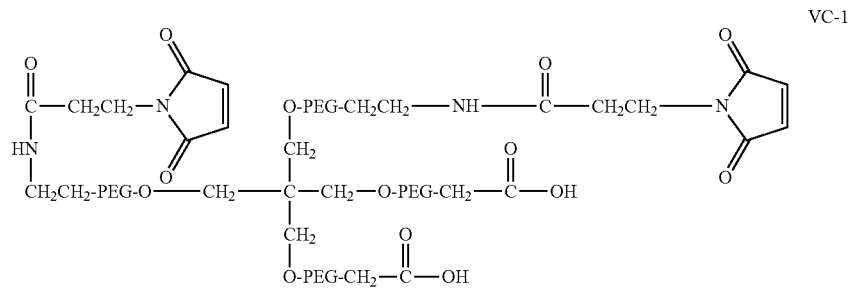

VC-1

The initial material is 4-arm (polyethylene glycol) amino—biacetic acid (VA-1) with the molecular weight of 10,000, and its synthetic steps are same as that of Example 9.

NMR (DMSO) δ: 2.32 (t, CH₂CH₂NH₂), 4.01 (s, CH₂COOH), 7.00 (s,

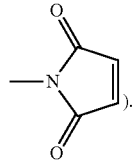
).

Example 12

4-Arm (Polyethylene Glycol)—Bimaleimide—biNHS Ester (VIA-1)

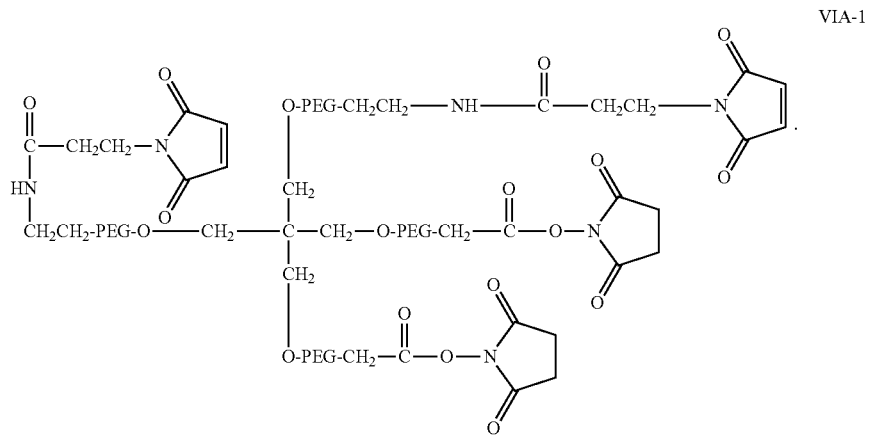

The initial material is 4-arm (polyethylene glycol)—bimaleimide—acetic acid (VC-1) with the molecular weight of 10,000, and its synthetic steps are same as that of Example 10.

NMR (DMSO) δ: 2.96 (t,

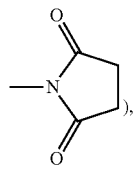
), 4.60 (s, CH₂COO), 7.00 (s,

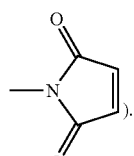
).

Example 13

4-Arm (Polyethylene Glycol) Acrylate—Single-Acetic Acid (VD-1)

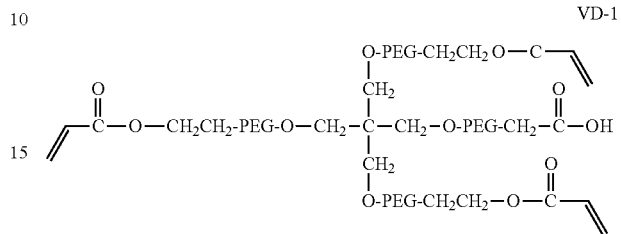

Procedure:

In three round-bottomed flask, inlet nitrogen, take 1.0 g molecular weight 10,000 four-arm polyethylene glycol hydroxy—single acetic acid (III-1) and 0.0005 gBHT, dissolved in 12 ml dichloromethane, heating steam 10% solvent, cooling to room temperature, add 49 ul triethylamine, stir for 5-10 minutes, add 250 ul acryloyl chloride, filling nitrogen, protected from light, the system is sealed and stirred, overnight reaction, the next day, concentrated at 30° C. to be thick, add 20 ml water dissolved to clear, put it aside for 30 minutes, add 15% sodium chloride, adjusted pH=2-3 with dilute hydrochloric acid, extracted with dichloromethane three times, combine organic phases, the organic phase was dried with anhydrous sodium sulfate to clarify, filter, concentrate filtrate at 30° C. to be thick, ice bath, add 20 ml isopropanol, thermal dissolution precipitation, filtration, wash with isopropanol, vacuum drying, get four-arm polyethylene glycol acrylate—single-acetic acid (VD-1).

NMR (DMSO) δ: 4.00 (s, CH₂COOH), 4.21 (t, CH₂OCOCH=CH₂), 5.93 (d, CH₂OCOCH=CH₂), 6.20 (q, CH₂OCOCH=CH₂), 6.36 (d, CH₂OCOCH=CH₂).

Example 14

4-Arm (Polyethylene Glycol) Acrylate—Single-NHS Ester (VII-1)

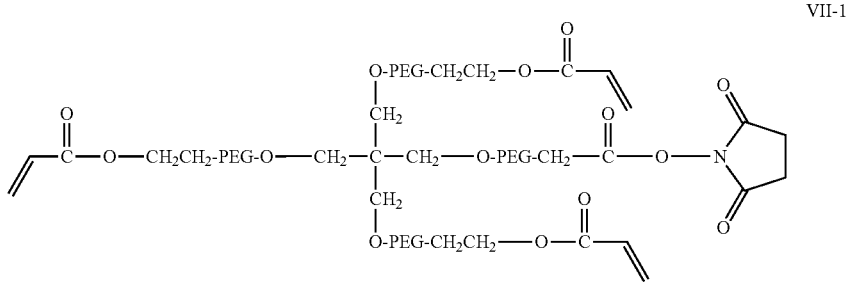

VII-1

Procedure:

In three round-bottomed flask, inlet nitrogen, dark, weighed 0.8 g molecular weight 10,000 four-arm polyethylene glycol acrylate-single-acetic acid (VD-1) and 0.011 gNHS, dissolved with 8 ml dichloromethane, add 0.0206 g DCC to system, dark airtight stirred overnight reaction, the next day, filter, concentrate the filtrate at 30° C. to be thick, stirring 30 minutes, in the ice bath after the heat dissolution with 16 ml isopropanol, precipitation, filtration, wash with isopropanol, vacuum drying, obtain four-arm polyethylene glycol acrylate—single-NHS ester (VII-1).

NMR (DMSO) δ: 2.86 (s,

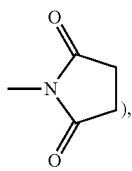

), 4.21 (t, $CH_2OCOCH=CH_2$), 4.60 (s, $CH_2COO$), 5.93 (b, $CH_2OCOCH=CH_2$), 6.20 (4, $CH_2OCOCH=CH_2$), 6.36 (b, $CH_2OCOCH=CH_2$).

Example 15

4-Arm Polyethylene Glycol Acrylic Acid—Acetic Acid (VE-1)

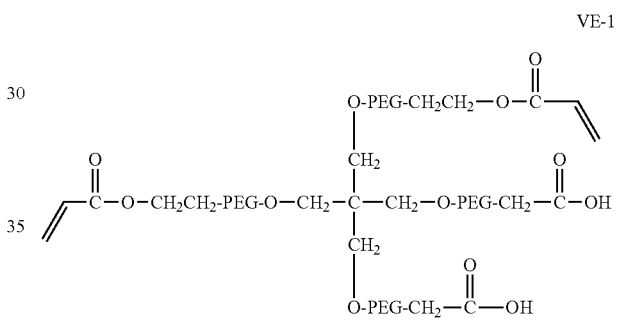

VE-1

The initial material is 4-arm (polyethylene glycol) hydroxy-biacetic acid (IIIA-1) with the molecular weight of 10,000, and its synthetic steps are same as that of Example 13.

NMR (DMSO) δ: 4.00 (s, $CH_2COOH$), 4.21 (t, $CH_2OCOCH=CH_2$), 5.93 (b, $CH_2OCOCH=CH_2$), 6.20 (4, $CH_2OCOCH=CH_2$), 6.36 (b, $CH_2OCOCH=CH_2$).

Example 16

4-Arm Polyethylene Glycol Acrylic Acid—bi NHS Ester (VIIA-1)

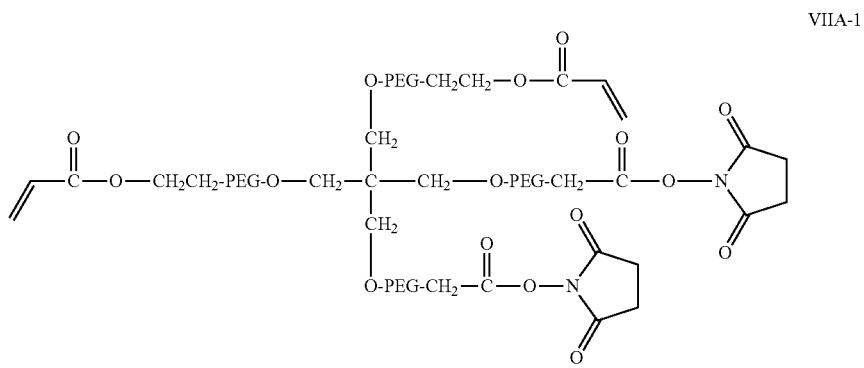

VIIA-1

The initial material is 4-arm (polyethylene glycol) acrylic acid—biacetic acid (VE-1) with the molecular weight of 10,000, and its synthetic steps are same as that of Example 14.

NMR (DMSO) δ: 2.86 (s,

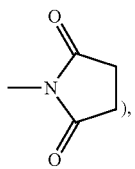

), 4.21 (t, CH$_2$OCOCH=CH$_2$), 4.60 (s, CH$_2$COO), 5.93 (d, CH$_2$OCOCH=CH$_2$), 6.20 (q, CH$_2$OCOCH=CH$_2$), 6.36 (d, CH$_2$OCOCH=CH$_2$).

Example 17

Synthesis of 8-Arm (Polyethylene Glycol) Hydroxy—Single Acetate (III-2) and 8-Arm (Polyethylene Glycol) Hydroxy—Diacetate (IIIA-2)

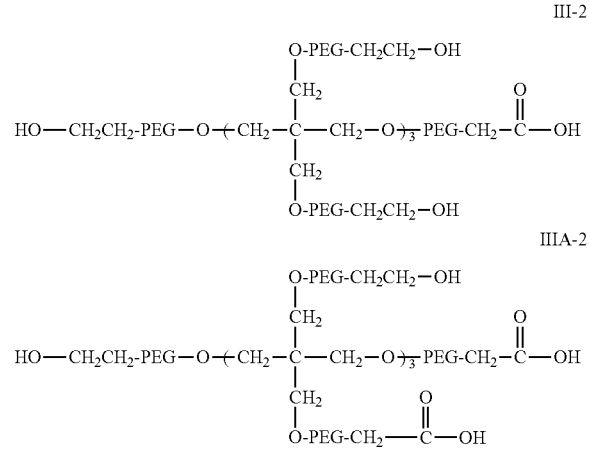

Procedure:

In three round-bottomed flask, inlet nitrogen, add 100 g 8ARM-PEG-10K and 800 mlTHF, heating dissolved, and steam about 20% solvents, cooling, add 8.96 g potassium tert-butyl alcohol, at room temperature for 2 hours, add dropping 10.34 ml bromine tert-butyl acetate, at room temperature overnight reaction, the next day filtratione, the reaction solution was concentrated to be thick, add 1000 ml alkaline hydrolyzate (1000 ml water, add 16.32 g sodium hydroxide and the 155.04 g sodium), 80° C. alkaline hydrolysis for 2 hours, 2N hydrochloric acid solution to adjust the pH to 2-3, add 15% sodium chloride solution, extracted with dichloromethane three times, combined organic extracts, dry with anhydrous sodium sulfate, filtered, 50° C., concentrated to be viscous, precipitate with ether and vacuum drying. 40 g crude product dubbed aqueous solution, DEAE anion column separation, respectively collected sodium chloride aqueous solution eluent, adjusted aqueous phase to pH 2-3 with 2N hydrochloric acid, extracted with dichloromethane, combined organic extracts, dryied with anhydrous sodium sulfate, filtered, concentrated, precipitated with diethyl ether, get molecular weight 10,000 eight-arm polyethylene glycol hydroxy—single-acetic acid (III-2) and eight-arm polyethylene glycol hydroxyl groups—acetic acid (IIIA-2), respectively.

NMR (DMSO) δ: 4.01 (s, CH$_2$COOH), 4.54 (t, CH$_2$OH).

Example 18

8-Arm Polyethylene Glycol Hydroxy—Single Methyl Acetate (IIIB-2)

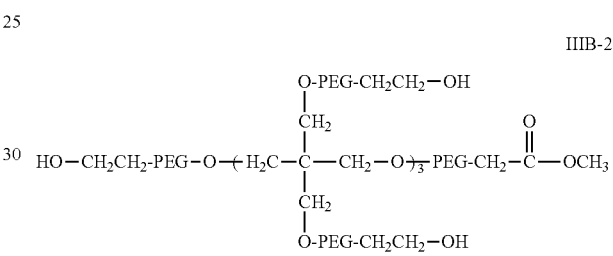

Procedure:

In single-port round-bottomed flask, add 4.0 g molecular weight 10,000 eight-arm polyethylene glycol hydroxy—single acid (111-2), dissolved in 20 ml anhydrous methanol, ice water bath, added 0.8 ml concentrated sulfuric acid at room temperature for 3 hours, with 8% aqueous solution of sodium bicarbonate to adjust the pH value of 7.0, extracted with dichloromethane three times, combined organic phases, the organic phase was dried with anhydrous magnesium sulfate, filtered, 40° C., concentrated to be viscous, precipitated with ether and vacuum drying, get the eight-arm polyethylene glycol hydroxy—single methyl acetate (IIIB-2).

NMR (DMSO) δ: 3.32 (s, CH$_2$COOCH$_3$), 4.13 (s, CH$_2$COOCH$_3$), 4.57 (t, CH$_2$OH).

Example 19

8-Arm Polyethylene Glycol Sulfonate—Single Methyl Acetate (IIIC-2)

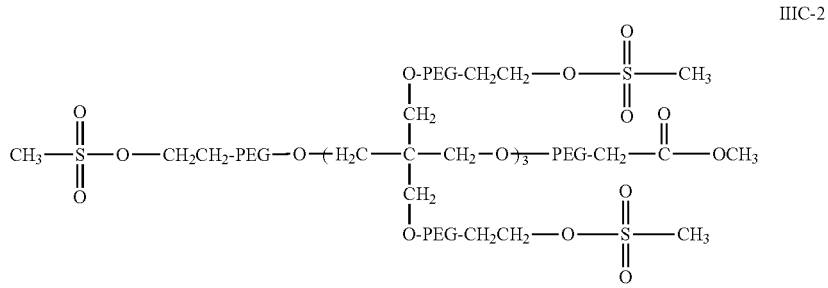

Procedure:

In three round-bottomed flask, inlet nitrogen, add 3.0 g molecular weight 10,000 eight-arm polyethylene glycol hydroxy—single methyl acetate, dissolved in 50 ml toluene, heat it to stream out 38 ml toluene, distillate to be clear, cool down to room temperature, add 5 ml dichloromethane, stirred for 10 minutes, add 439 ul triethylamine, stirred 5 minutes, add dropping 220 ul methyl chloride, sealed reaction overnight, the next day, add 1.44 ml ethanol, stirring for 15 minutes, filtered, concentrated to be viscous, heat dissolved with 60 ml isopropanol, ice water bath, sedimentate, filtrate, wash cake with isopropanol one time, vacuum drying, get eight-arm polyethylene glycol sulfonate—single methyl acetate (IIIC-2).

NMR (DMSO) δ: 3.17 (s, CH$_2$OSO$_2$CH$_3$), 4.13 (s, CH$_2$COOCH$_3$), 4.30 (t, CH$_2$OSO$_2$CH$_3$).

Example 20

Synthesis of 8-Arm Polyethylene Glycol Amino—Single-Acetic Acid (V-2)

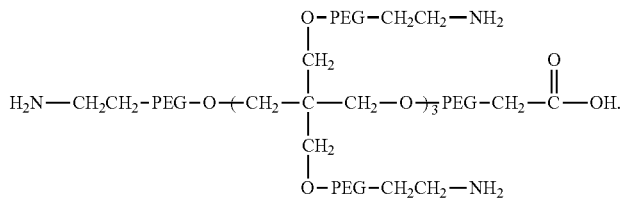

Procedure:

In single-port round-bottomed flask, add 2.6 g molecular weight 10,000 eight-arm polyethylene glycol sulfonate—single methyl acetate, dissolved in 7.8 ml degassed water, use 2N aqueous sodium hydroxide to adjust the solution pH 12.0, at room temperature for 2-2.5 hours, add 26 ml ammonia solution dissolved 1.3 g ammonium chloride to the system, at room temperature stirred for 72 hours, after the reaction, add 7 g sodium chloride, dissolved, extracted with methylene chloride reaction mixture three times, combine organic phase, concentrated at 40° C. to dryness, add 30 ml water, stirring to dissolve to clear, adjust the pH to 2-3 with 2N hydrochloric acid, add 5 g sodium chloride, again extracted with dichloromethane three times, and combined organic phases, the organic phase with anhydrous sodium sulfate to dry to clarify, filter, concentrated at 40° C. to be viscous, sedimentation with 50 ml ether, filtration, vacuum drying, get eight-arm polyethylene glycol amino—single-acetic acid (V-2).

NMR (DMSO) δ: 2.96 (t, CH$_2$CH$_2$NH$_2$), 4.00 (s, CH$_2$COOH).

Example 21

Synthesis of 8-Arm Polyethylene Glycol Acrylate—Single-Acetic Acid (VI-2)

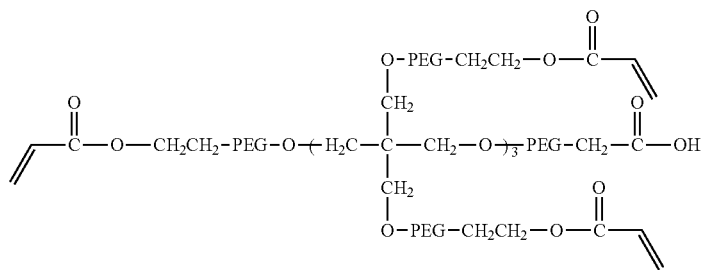

Procedure:

In three round-bottomed flask, inlet nitrogen, take 1.0 g molecular weight 10,000 eight-arm polyethylene glycol hydroxy—single acetic acid (III-2) and 0.0005 gBHT, dissolved in 12 ml dichloromethane, heating to steam out 10% solvent, cooling to room temperature, add 115 ul triethylamine, stirring for 5-10 minutes, adding 59 ul acryloyl chloride, filling nitrogen, protect from light, confined system, overnight reaction with stirring, the next day, concentrated at 30° C. to be thick, add 20 ml, dissolved to clear, put it aside for 30 minutes, adding 15% sodium chloride, to adjust pH=2-3 with dilute hydrochloric acid, extracted with dichloromethane three times, combine organic phases, the organic phase was dried with anhydrous sodium sulfate to clarify, filter, concentrated filtrate to be thick at 30° C., ice bath add 20 ml isopropanol, thermal dissolution and precipitation, filtration, wash with isopropanol, vacuum drying, get eight-arm polyethylene glycol acrylate—single-acetic acid (VI-2).

NMR (DMSO) δ: 4.00 (s, $CH_2COOH$), 4.21 (t, $CH_2OCOCH=CH_2$), 5.93 (d, $CH_2OCOCH=CH_2$), 6.20 (q, $CH_2OCOCH=CH_2$), 6.36 (d, $CH_2OCOCH=CH_2$).

Example 22

The Synthesis of 8-Arm Polyethylene Glycol Acrylate—Single-NHS Ester (VII-2)

4.21 (t, $CH_2OCOCH=CH_2$), 4.60 (s, $CH_2NHS$), 5.93 (d, $CH_2OCOCH=CH_2$), 6.20 (q, $CH_2OCOCH=CH_2$), 6.36 (d, $CH_2OCOCH=CH_2$).

Example 23

Conjugates Combined by Eight-Arm Polyethylene Glycol Acrylate-Single-Acetic Acid (VI-2) and Enoxaparin Derivatives 1 gram molecular weight 10,000 eight-arm polyethylene glycol acrylate-single-acetic acid (VI-2) (produced in Implementation Example 21) was dissolved in 10 ml dichloromethane, and then add 0.12 g enoxaparin topotecan glycine cool (Glycine-Irinotecan) (Irinotecan purchased from Chengdu Furunde Industrial Co., Ltd.), and 50 mg dimethylaminopyridine, and 95 mg dicyclohexylcarbodiimide two sub-15 amine. This solution was stirred at room temperature for 6 hours, vacuum to recover solvent, and add 20 ml 1,4-dioxane to the residue to dissolve. Filter to remove the precipitate, the solution is concentrated, the residue by adding 20 ml ether and filtered to collect precipitation and then vacuum drying with ether. Yield: 0.8 g (80%), melting point: 46-50° C.

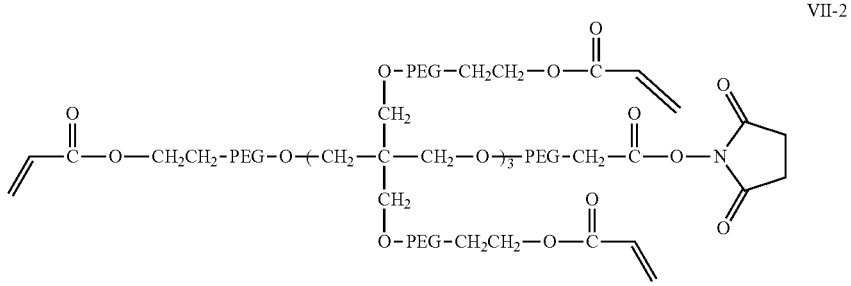

VII-2

Procedure:

8-arm poly(ethylene glycol) acrylate—single-acetic acid (VI-2) (10 kDa, 0.8 g) and N-hydroxysiccinimide (0.011 g) were dissolved in 8 ml of dichloromethane. DCC (0.0206 g) was added and the solution was stirred overnight at room temperature, filtered, concentrated under vacuum at 40° C. The residue iso-propanol and then crystallized by cooling the solution to 0° C. The resulting precipitate was collected, washed with iso-propanol and dried to afford the 4-arm poly(ethylene glycol) acrylate—single-N-hydroxysuccinimidyl ester (VII-2).

NMR (DMSO) δ: 2.86 (s,

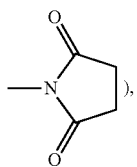

),

Example 24

Synthesis of Stable Eight-Arm Polyethylene Glycol Acrylate with Drug Gel

Eight-arm polyethylene glycol acrylate—single-acetic acid (VI-2) (10 k Da, 0.5 g) and enoxaparin derivatives (prepared in Example 23) were dissolved in 10 ml phosphate buffer (pH7.4). 4-arm polyethylene glycol SH (5 k Da, 0.4 g) was dissolved in 10 ml phosphate buffer (pH 7.4). The two solutions were mixed quickly, and the eight-arm polyethylene glycol gel formed in 2 minutes. The formed gel was placed in 100 ml phosphate buffer (pH 7.4), stored at 37° C. The gel will be stable in 360 days, and will witness and degeneration or melting, but the enoxaparin will release slowly.

The invention claimed is:

1. A multi-arm poly(ethylene glycol) derivative, wherein said multi-arm poly(ethylene glycol) derivative is a multi-arm poly(ethylene glycol) amino-single-acetic acid of formula V:

V
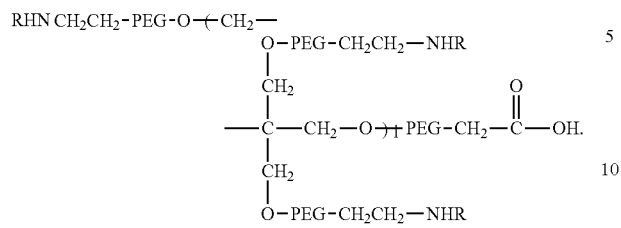
wherein, wherein R is a residue of Irinotecan;
PEG is —$(CH_2CH_2O)_m$—, which is the same or different from one another, the mean of m is an integer selected from 2 to 250; and
l is 2 or 3.
2. The multi-arm poly(ethylene glycol) derivative of claim 1, wherein said multi-arm poly(ethylene glycol) has a molecular weight between about 400 Dalton and about 80,000 Dalton.
* * * * *